United States Patent
Kawama et al.

(10) Patent No.: US 6,673,382 B2
(45) Date of Patent: Jan. 6, 2004

(54) IRON-CONTAINING PROTEIN COMPOSITION

(75) Inventors: Toshihiro Kawama, Saitama (JP); Kaoru Sato, Saitama (JP); Akihito Ikenaga, Saitama (JP)

(73) Assignee: Snow Brand Milk Products Co., Ltd., Hokkaido (JP)

( * ) Notice: Subject to any disclaimer, the term of this patent is extended or adjusted under 35 U.S.C. 154(b) by 135 days.

(21) Appl. No.: 09/884,361

(22) Filed: Jun. 19, 2001

(65) Prior Publication Data

US 2002/0012723 A1 Jan. 31, 2002

(30) Foreign Application Priority Data

Jun. 20, 2000 (JP) ......................................... 2000-184731

(51) Int. Cl.[7] .................................................. A23L 2/38

(52) U.S. Cl. ........................ 426/74; 426/321; 426/327; 426/334; 426/524; 426/443; 426/548; 426/590; 426/656; 426/661

(58) Field of Search .......................... 426/74, 321, 327, 426/334, 524, 656, 661, 548, 448, 590

(56) References Cited

U.S. PATENT DOCUMENTS

| 4,214,996 A | * | 7/1980 | Buddemeyer et al. ......... 252/1 |
| 4,351,735 A | * | 9/1982 | Buddemeyer et al. ......... 252/1 |
| 4,806,343 A | * | 2/1989 | Carpenter et al. .......... 424/450 |
| 5,364,642 A | * | 11/1994 | Altura et al. ................. 426/74 |
| 5,436,024 A | * | 7/1995 | Rogols ....................... 426/643 |
| 5,436,025 A | * | 7/1995 | Rogols et al. .............. 426/643 |
| 5,456,938 A | * | 10/1995 | Rogols ....................... 426/643 |
| 5,917,021 A | | 6/1999 | Lee |
| 6,261,610 B1 | * | 7/2001 | Sher et al. .................... 426/74 |

FOREIGN PATENT DOCUMENTS

| EP | 0 316 709 A2 | 5/1989 |
| EP | 1 040 766 A1 | 10/2000 |

\* cited by examiner

*Primary Examiner*—Carolyn Paden
(74) *Attorney, Agent, or Firm*—Knobbe Martens Olson & Bear, LLP

(57) ABSTRACT

Addition of a specific sugar compound to an iron-containing protein composition solution can provide an excellent freezing and thawing stability and restrained precipitate productivity in a thawed solution of its frozen product and increase the efficiency in the use of the iron-containing protein useful for enrichment of iron in a food or drink, production of iron preparations.

16 Claims, 1 Drawing Sheet

IRON-CONTAINING PROTEIN COMPOSITION

FIELD OF THE INVENTION

The present invention relates to an iron-containing protein composition solution which is superior in freezing-thawing stability and low in precipitating tendency when frozen and thawed; a frozen product of the solution; a liquid composition obtained by thawing the frozen product; and a powder obtained by drying the solution or the liquid composition. The iron-containing protein composition solution of the present invention has an excellent adaptability for freezing to storage or transfer it in the frozen state. This composition solution has restrained precipitate productivity in the solution obtained by thawing a frozen product of the composition solution. The composition solution has no astringent taste uniquely possessed by iron. Therefore, the composition solution can be suitably used in production of an iron-enriched food or drink or an iron preparation. This composition solution is also useful for prevention or treatment of anemia.

DESCRIPTION OF THE RELATED ART

Since 1975, the iron intake by Japanese has been flat at a sufficiency ratio of about 100% relative to the iron requirement. Iron is important -for maintenance of the homeostasis of human body and is one of the nutrients to be taken with care in meals. The iron sufficiency ratio particularly in young to middle aged women is between 80 to 90%, and the iron shortage in these women is pointed out in "Status of National Nutrition, 1998 Edition", published by Daiichi Shuppan K. K. Thus, many of the young to middle aged women suffering from iron shortage or anemia are supplementing iron in the form of iron-enriched food or drink or of medicine such as iron preparation or the like.

However, inorganic irons used in iron preparations, such as iron citrate, iron pyrophosphate, iron sulfate and the like generally have an astringent taste or a metallic taste, both uniquely possessed by iron, or have harmful side effects such as damages to stomach, intestines and mucosa in some cases. Heme iron, which is an organoiron, has a problem of possessing a metallic taste, a raw fish-like smell, etc. although it is highly absorbable. Therefore, when the above iron preparations are added to a food or a drink or are used as such, there are cases that the addition amount must be restricted in some cases, often making it difficult to intake the required amount.

Meanwhile, as iron-containing proteins, an iron-lactoferrin complex (Japanese Patent Laid-Open (Kokai) No. 304798/'95), an iron-casein complex (Japanese Patent Laid-Open (Kokai) No. 77793/'97), etc. are known in the form of a composition. These iron-containing protein compositions are free from astringent taste or metallic taste uniquely possessed by iron, have no harmful side effects, and moreover are superior in solubility and thermal stability; therefore, they are suited for use in foods, drinks and iron preparations.

Incidentally, one of the present inventors filed as a co-inventor an Japanese Application No. 89741/99 concerning an iron-whey protein complex, which is published as Japanes Patent Laid-Open (Kokai) No. 279143/2000.

SUMMARY OF THE INVENTION

As describe above, iron-containing protein compositions are being used in foods, drinks and iron preparations. However, they may have a problem in generating precipitate when a solution of these compositions is frozen for storage, transfer or the like and then thawed.

One of the objects of present invention is to provide a solution containing an iron-containing protein composition useful for iron enrichment in foods and drinks or as an effective ingredient of iron preparation, which solution has restrained precipitate productivity after freezing and thawing. The other object of the present invention is to provide a frozen product of the above solution and a solution obtained by thawing the frozen product, both useful for iron enrichment in foods and drinks as well as for production of iron preparation.

The present inventors proceeded with a study in view of the above objects. As a result, the present inventors found out that precipitation in a resulting solution by thawing a frozen product of the original solution of the iron-containing protein composition, can be suppressed by adding at least one compound selected from monosaccharides, disaccharides, sugaralcohols, non-reducing saccharides and dextrin to the original solution. The present invention has been completed based on this above findings.

In the present invention, "superior in freezing-thawing stability" refers to that, when a sample of an iron-containing protein composition solution is placed in an appropriate container and stored in a frozen state at $-20°$ C. for 2 weeks, then the frozen sample is thawed, for example, by contacting the container with a flowing water or by allowing the container to stand at room temperature, and 50 ml of the thawed sample is taken into a 50-ml graduated test tube and subjected to centrifugation at 3,000 rpm for 15 minutes using a centrifuge (Kubota Ks-5000P), the volume of the precipitate generated in the centrifuged sample is 0.5 ml or less. When the volume of the precipitate generated is as small as above, the loss of iron-containing protein by precipitation is suppressed effectively; the thawed solution has a good quality for use in a food, a drink or an iron preparation; and its storability and transferability in a frozen state, etc. can give an improved economic efficiency.

The present invention can provide an iron-containing protein composition solution which has restrained precipitate productivity after freezing and thawing, and superior freezing-thawing stability. The iron-containing protein composition solution according to the present invention has no astringent taste uniquely possessed by iron and, therefore, can be suitably used in production of an iron-enriched food or drink or an iron preparation and is useful for prevention or treatment of anemia.

DETAILED DESCRIPTION OF THE INVENTION AND PREFERRED EMBODIMENTS

Figure 1:
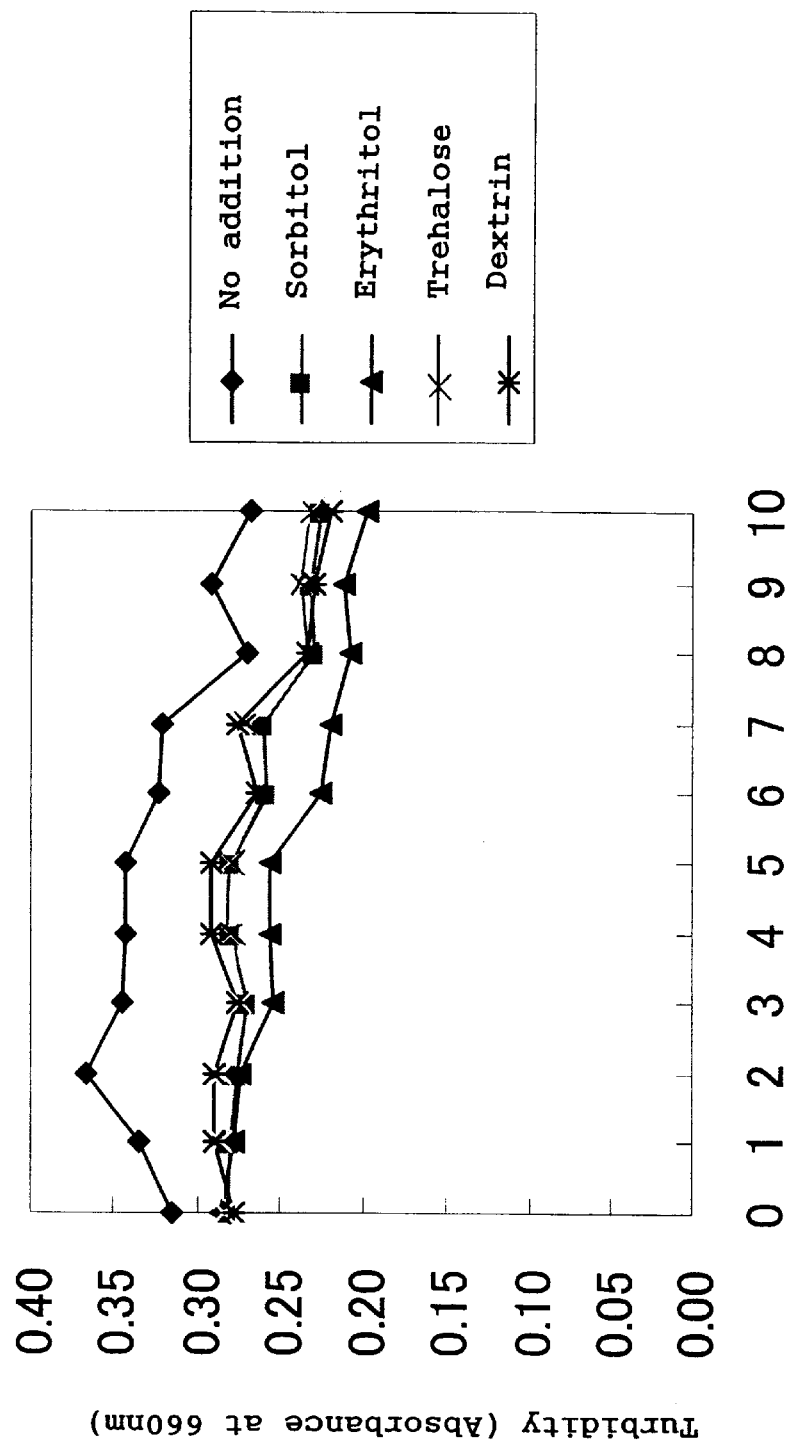
FIG. 1 is a graph showing the change of turbidity of samples when they were subjected to repeated freezing-thawing operations in Example 2. The numbers 0 to 10 means the repeat times of a unit operation including freezing of a solution and thawing of the resultant frozen product.

A iron-containing protein composition solution, i. e., a solution containing an iron-containing composition, according to the present invention is a solution of an iron-containing protein composition in an aqueous medium and has excellent freezing-thawing stability. The iron-containing protein composition is a soluble and dispersible agglomerate, or aggregate, obtained by allowing iron to act on a protein.

As an example of the iron-containing protein composition, there can be mentioned a composition containing mainly a reaction product (soluble and dispersible agglomerates or aggregates) obtained by mixing iron, protein and at least one of a carbonate and a bicarbonate.

When the iron-containing composition is added to an aqueous medium, the components comprising the protein are dispersed as particles in the aqueous medium and the water-soluble mineral components are dissolved in the aqueous medium. Therefore, the composition forms fine particles comprising the protein(s) in an aqueous medium which are dispersible therein.

Incidentally, as the aqueous medium, a medium composed mainly of water can be mentioned. Ordinarily, water is used as the aqueous medium, per se, and an aqueous solution of the iron-containing protein composition is formed.

The aqueous solution of an iron-containing protein composition can be obtained when water is used as the aqueous medium, by, for example, preparing a solution containing at least either of a carbonate and a bicarbonate (as a solution A), a solution containing iron (as a solution B) and a solution containing a protein (as a solution C) and mixing these solutions A to C to allow the individual components to act on each other. In this case, the molar concentration of iron ion in the solution B is $1/3$ or less, preferably $1/10$ or less, more preferably $1/30$ or less, further preferably $1/60$ or less, most preferably $1/100$ or less of the molar concentration of carbonate ion and/or bicarbonate ion dissolved in the solution A (the total molar concentration of both the carbonate ion and the bicarbonate ion is used when both the carbonate ion and the bicarbonate ion are present). The preferable lower limit of the ratio of the molar concentration of iron (A) to that of the molar concentration (B) of carbonate ion and/or bicarbonate ion, i.e., A/B is $1/10,000$.

The molar concentration of protein in the solution C is preferably $1/2$ to $1/1,000$ of the molar concentration of iron ion in the solution B. Incidentally, when there is used, as the protein in the solution C, a protein decomposition product obtained by proteolysis, its molar concentration can be the molar concentration of the protein before proteolysis and is preferably $1/2$ to $1/1,000$ of the molar concentration of iron ion in the solution B.

The solution B and the solution C may be prepared separately and mixed with the solution A. Alternatively, the solutions A and C may be first mixed and the resultant mixture may be mixed with the solution A. In these cases, the solution containing a protein is preferably added before the solution containing iron is added, in order for the mixed solution to have higher stability. The reaction between carbonate and/or bicarbonate, iron and protein takes place in the mixed solution. Either of the iron and the protein to be added may be used in a solid form.

Further, in order to keep a high concentration of carbonate ion and bicarbonate ion in the mixed solution, the solution A may be allowed to contain a carbonate and/or a bicarbonate in an amount exceeding the solubility. For the same purpose, when a mixture of the solutions B and C is used, a carbonate and/or a bicarbonate, or a carbonate solution and/or a bicarbonate solution may be added in the middle point of the mixing process by adding the mixture of the solutions B and C to the solution A, i.e., at a timing when part of the mixture of the solutions B and C has been added to the solution A.

The solution of an iron-containing protein composition can also be obtained by mixing a solution containing a protein and at least one of a carbonate and a bicarbonate (as a solution D) and a solution containing iron (as a solution E) to give rise to a reaction between them. In this case, the molar concentration of iron ion in the solution E is $1/3$ or less, preferably $1/10$ or less, more preferably $1/30$ or less, further preferably $1/60$ or less, most preferably $1/100$ or less of the molar concentration of at least one of carbonate ion and bicarbonate ion dissolved in the solution D (the total molar concentration of carbonate ion and bicarbonate ion is used, when both the carbonate ion and the bicarbonate ion are present). The preferable lower limit of the ratio of the molar concentration of iron (A) to that of the molar concentration (B) of carbonate ion and/or bicarbonate ion, i.e., A/B is $1/10,000$.

The molar concentration of protein in the solution D is preferably $1/2$ to $1/1,000$ of the molar concentration of iron ion in the solution E. Incidentally, when there is used, as the protein in the solution D, a protein decomposition product obtained by proteolysis, its molar concentration can be the molar concentration of the protein before proteolysis and is preferably $1/2$ to $1/1,000$ of the molar concentration of iron ion in the solution E.

Then, the solution of an iron-containing protein composition is sterilized or pasteurized. The solution may be concentrated, if required. The resultant solution is then subjected to particle diameter adjustment to preferably 50 nm or less. To the resulting solution is added a saccharide for imparting freezing-thawing stability to the solution; then, pH adjustment is made; thereby, the desired iron-containing protein composition solution superior in freezing-thawing stability can be obtained. This solution, when filled in an appropriate container, can be stored or transferred in a frozen state, and, in the solution after thawing, almost no precipitate is generated or the amount of precipitate generated is effectively very small.

The pasteurization and sterilization can be conducted according to an conventional method, for example, by heat pasteurization, sterilization, or bacteria removal by microfiltration (MF). Heat pasteurization can be conducted, for example, by low-temperature pasteurization of about 65° C. for 30 minutes or high-temperature short-time pasteurization at about 120° C. for 2 to 3 seconds.

The concentrating treatment is useful for enhancement of iron concentration in the final product and can be conducted, for example, by a method using a membrane such as ultrafiltration (UF) membrane, nanofiltration (NF) membrane, reverse osmosis (RO) membrane or the like, or by vacuum concentration. Besides the concentration, adjustment of iron concentration to a desired level is also possible by subjecting the iron-containing protein composition solution to spray-freezing, freeze-drying or the like according to an conventional method to powderize the solution and diluting the powder to obtain an appropriate concentration in a solution using water or the like.

The iron-containing protein composition is dissolved in an aqueous medium in the form of particles. The diameters of the particles are adjusted to preferably 200 nm or less, i.e., at most 200 nm, in terms of average particle diameter, by subjecting the above solution to a homogenization treatment at 100 kg/cm$^2$ or more, preferably at 300 kg/cm$^2$ or more, or by using a MF membrane of 400 nm. The average particle diameter is preferably 50 nm or less and, when the average particle diameter of the iron-containing protein composition is at such a level, the composition can have even higher stability.

When the concentration, the drying and the adjustment of average particle diameter are conducted, these treatments can be conducted at any timing after preparation of an iron-containing protein composition solution (this may contain or may not contain a saccharide). When heat pasteurization is conducted, however, the above treatments are conducted preferably after the heat pasteurization.

As the protein used in preparation of an iron-containing protein composition, there can be mentioned lactoferrins, casein proteins, whey proteins, etc. At least one selected from these proteins can be used.

As the lactoferrins, there can be mentioned, for example, lactoferrins separated from liquid secretions (e.g. milks) of mammals such as human, cattle and the like; transferring separated form blood, internal organs, etc.; lactoferrins (e.g. ovotransferrins) separated form egg, etc.; and decomposition products obtained by enzymatic decomposition of these lactoferrins. As the casein proteins, there can be mentioned, for example, casein proteins separated from liquid secretions (e.g. milks) of mammals (e.g. human and cattle), such as casein, acid casein, casein sodium, lactic acid casein, α-casein, β-casein, κ-casein and the like; and decomposition products obtained by enzymatic decomposition of these caseins. As the whey proteins, there can be mentioned, for example, decomposition products obtained by enzymatic decomposition of whey proteins separated from liquid secretions (e.g. milks) of mammals such as human, cattle and the like. There can be mentioned decomposition products obtained by subjecting a whey protein to component separation to isolate individual components such as β-lactoglobulin, α-lactoalbumin and the like and then subjecting each component to enzymatic decomposition. A number of methods are known for separation of these proteins in a large quantity. A protein separated according to any method is usable in the present invention. A protein produced by a microorganism, animal cells or a transgenic animal by genetic engineering is also usable.

Incidentally, when there is used, as the casein protein, a casein mixture (e.g. crude casein) of α-casein, β-casein and κ-casein, the average molecular weight of the caseins in the mixture is determined from the proportions of individual protein components, from which the molar concentration of the casein dissolved can be calculated.

When there is used, as the whey protein, a mixture of various protein components, the average molecular weight of the protein components in the mixture is determined from the proportions of individual protein components, from which the molar concentration of the whey protein dissolved can be calculated.

When a preparation containing various protein components or a hydrolysis product thereof is used, each of which is a mixture of protein components of different molecular weights, the protein molar concentration can be calculated by the step of measuring the proportions and molecular weights of the individual protein components in the same manner as described above, according to, for example, electrophoresis using a gel medium; calculating the average molecular weight of the protein components based on the measured proportions and molecular weights; and calculating the protein molar concentration of the mixture based on the average molecular weight and the total amount of each protein component.

Meanwhile, the enzymatic decomposition product of a lactoferrin, a casein protein or a whey protein can be obtained by using a protease. As the protease, there can be used, for example, enzymes obtained from animals, such as trypsin, chymotrypsin, pepsin and the like; enzymes obtained from plants, such as papain, bromelain, ficin and the like; and enzymes obtained from microorganisms (e.g. mold, bacteria and yeast). As the form of enzyme when the enzyme is allowed to act on a protein, there can be mentioned an isolated and purified enzyme; a crude enzyme; a cultured product of a microorganism containing an enzyme; an enzyme-containing material obtained by removing the microorganism from the above cultured product; microorganism cells or a crushed product thereof; a recombinant protease; and so forth. As such an enzyme, there can be used those prepared from various materials, or commercial enzyme preparations. As the enzymatic decomposition product, there is preferred, for example, one contains decomposition products having molecular weights in a range not exceeding 10,000.

As the iron used in preparation of an iron-containing protein composition, there can be mentioned, for example, iron salts mostly of trivalency which show a pH of 4 or less when dissolved in deionized water, such as ferric chloride, ferric nitrate, ferric sulfate and the like.

As the solution containing at least one of a carbonate and a bicarbonate, there can be mentioned, for example, a carbonic acid water, an ammonium bicarbonate solution, a sodium bicarbonate solution, a potassium bicarbonate solution, a sodium carbonate solution, a calcium carbonate solution and a mixture of two or more of these solutions. To these solutions is preferably added, as a pH-adjusting agent, sodium hydroxide, ammonia, potassium hydroxide, hydrochloric acid, citric acid, lactic acid or the like.

As the saccharide added for securing freezing-thawing stability, there can be mentioned, for example, monosaccharides such as grape sugar, fruit sugar and the like; disaccharides such as cane sugar, milk sugar and the like; sugaralcohols such as sorbitol, maltitol, erythritol and the like; non-reducing saccharides such as trehalose, palatinit, reduced thick malt syrup and the like; and dextrin. Of these, particularly preferred are sugaralcohols, non-reducing saccharides and dextrin. At least one kind selected from the above monosaccharides, disaccharides, sugaralcohols, non-reducing saccharides and dextrin is added to the iron-containing protein composition solution in an amount of preferably 3 to 50% by weight in order to more effectively suppress not only precipitation in the resulting solution obtained by thawing a frozen product of the solution of the iron-containing protein composition, but also increase of viscosity of the resulting solution which may reduce its workability.

When pH adjustment is carried out after a saccharide has been added to the iron-containing protein composition solution, the pH of the resulting solution is adjusted to preferably 5 to 10, more preferably 5.8 to 8.5, in order to more effectively suppress not only separation of iron ion during the storage, resulting in deteriorated taste, but also generation of lysinoalanine. For this pH adjustment, there can be used, for example, sodium hydroxide, ammonia, potassium hydroxide, hydrochloric acid, citric acid, or lactic acid.

The iron-containing protein composition solution of the present invention can be filled in an appropriate container to use as a product. The filled product can be frozen according to an conventional method and the frozen product can be stored and transferred. The frozen product can be thawed into a solution and can be favorably used for production of an iron-containing drink, iron enrichment of a food or a drink, or production of an iron preparation.

The iron-containing protein composition solution of the present invention is superior in freezing-thawing stability; therefore, when thawed from a frozen state, the solution has no precipitate or a very small amount of a precipitate. As a result, the loss of the iron-containing protein in the solution can be prevented and the efficiency in the use of iron-containing protein can be strikingly increased.

The iron-containing protein composition solution and the liquid composition obtained by thawing the frozen product of the iron-containing protein composition solution, according to the present invention, can be made into a powdery product via an conventional drying process. The period and efficiency in the storage and transfer of the iron-containing composition can be more greatly improved by combining the storage or transfer in the frozen state and the storage or transfer in the powder state.

EXAMPLES

The present invention is described in more detail below by way of Examples.

Example 1

Solution F:

A solution obtained by dissolving 0.92 mM of lactoferrin (a product of TATUA) in 4.02 kg of an aqueous solution containing 3.1 M of sodium bicarbonate. Solution G:

43.6 kg of an aqueous solution containing 0.46% by weight (17 mM) of ferric chloride.

The solution F and the solution G were mixed. The mixed solution was heat-pasteurized at 70° C. for 18 minutes and then concentrated to 1/20 using an UF membrane to obtain 2.2 kg of a concentrate of an iron-containing protein composition solution. The concentrate was subjected to a homogenization treatment of 500 kg/cm². The resulting concentrate was divided into five portions each of 400 g. To the four portions was added 80 g of sorbitol, erythritol, trehalose and dextrin, respectively, and nothing was added to the remaining one portion.

Each of the thus-prepared five samples was evaluated for freezing-thawing stability and measured for average particle diameter, as follows.

Evaluation of freezing-thawing stability

Each sample was stored in a frozen state at −20° C. for 2 weeks. The resulting frozen samples were thawed on a flowing water. Each 50 ml of the thawed sample was placed in a 50-ml graduated test tube and subjected to centrifugation at 3,000 rpm for 15 minutes using a centrifuge (Kubota ks-5000P) to measure the volume of the precipitate generated. In the present invention, when the volume of the precipitate generated was 0.5 ml or less, the solution (the sample) was regarded as "superior in freezing-thawing stability".

Measurement of average particle diameter

This measurement was conducted at a sample temperature of 25° C. using a light-scattering photometer (Autosizer 4700, Malvern Instrument Ltd. UK) and an argon laser of 488 nm (Air-Cooled Argon Ion Laser System, Model 2031, Uniphase, California).

The results are shown in Table 1.

TABLE 1

|  | Sorbitol | Erythritol | Trehalose | Dextrin | No addition |
|---|---|---|---|---|---|
| Precipitate (ml) | 0.1 | 0.1 | 0.1 | 0.1 | 2.0 |
| Average particle diameter (nm) | 38.3 | 34.5 | 36.2 | 35.8 | 330.6 |

As is clear from Table 1, it was confirmed that freezing-thawing stability can be imparted to an iron-containing protein composition solution by adding thereto a sugaralcohol, a non-reducing saccharide or dextrin.

Example 2

Solution H:

450 kg of an aqueous solution containing 5% by weight (0.6 M) of sodium bicarbonate.

Solution I:

50 kg of an aqueous solution containing 10% by weight (1.25 mM) of lactoferrin (a product of DMV)

Solution J:

740 kg of an aqueous solution containing 0.5% by weight (18.5 mM) of ferric chloride.

The solution H and the solution I were mixed. To the mixed solution was added the solution J. The resulting mixed solution was heat-pasteurized by heating up to 80° C. The pasteurized solution was concentrated to 1/25 using a rotary evaporator (RE-10ED-120, a product of Shibata Kagaku), to obtain 48 kg of a concentrate of an iron-containing protein composition solution. The concentrate was subjected to a homogenization treatment of 300 kg/cm². The resulting concentrate was divided into five portions each of 9 kg and each portion was placed in a container. To the four portions were added 1.9 kg of sorbitol, erythritol, trehalose and dextrin, respectively, and nothing was added to the remaining one portion.

Each of the five samples was stored in a frozen state at −20° C. for 2 days and then thawed by contacting the outer wall of the container with a flowing water. The thawed sample was measured for turbidity. Thereafter, the sample was again stored in a frozen state at −20° C. for 2 days and thawed using a flowing water. This operation of freezing and thawing was repeated 10 times, and turbidity measurement was conducted after each operation.

The turbidity measurement was conducted as follows: The sample after 10 times of the freezing and thawing operations was evaluated for freezing-thawing stability and measured for average particle diameter, according to the same methods as in Example 1.

Measurement of turbidity

A sample was diluted ten-fold with deionized water and measured for absorbance at 660 nm using a spectrophotometer (U-2000, a product of Hitachi Ltd.). The absorbance was taken as the turbidity of the sample.

The results are shown in Table 2 and FIG. 1.

TABLE 2

|  | Sorbitol | Erythritol | Trehalose | Dextrin | No addition |
|---|---|---|---|---|---|
| Precipitate (ml) | 0.1 | 0.1 | 0.1 | 0.1 | 2.3 |
| Average particle diameter (nm) | 39.2 | 35.7 | 35.9 | 37.0 | 320.8 |

As is clear from Table 21, it was confirmed that freezing-thawing stability can be imparted to an iron-containing protein composition solution by adding thereto a sugaralcohol, a non-reducing saccharide or dextrin.

Regarding the results in FIG. 1, it was confirmed that an iron-containing protein composition solution to which a sugaralcohol, a non-reducing saccharide or dextrin has been added, as compared with the same solution to which the above material is not added, is low in turbidity and very small in precipitate amount.

Example 3

Solution K:

Two liters of an aqueous solution containing 2 M of sodium bicarbonate and 16 μM of α-casein (a product of Sigma).

Solution L:

Two liters of an aqueous solution containing 2.4 mM (as iron ion) of ferric sulfate.

The solution K and the solution L were mixed to obtain a mixed solution. The mixed solution was subjected to desalting and concentration using an UF membrane (molecular weight cutoff: 5,000) to obtain 0.4 kg of a concentrate of an iron-containing protein composition solution.

The concentrate was diluted with a buffer solution of pH 7.5 containing 0.05 M/l of imidazole and 0.15 M/l of sodium chloride so that the iron ion concentration after dilution became 27 mg/100 ml. The diluted solution was placed in a test tube with a screw head. The test tube was sealed, heated at 90° C. for 10 minutes, allowed to cool to room temperature, and subjected to a homogenization treatment at 300 kg/cm$^2$. There were prepared two kinds of samples, that is, a sample obtained by adding 2 g of dextrin to 50 ml of the solution after the above homogenization treatment and a sample which was the solution after the homogenization treatment per se.

The thus-prepared two samples were evaluated for freezing-thawing stability and measured for average particle diameter, according to the same methods as in Example 1. The results are shown in Table 3.

TABLE 3

|  | Dextrin | No addition |
|---|---|---|
| Precipitate (ml) | 0.1 | 3.0 |
| Average particle diameter (nm) | 33.6 | 360.4 |

From the results of Table 3, it was confirmed that freezing-thawing stability can be imparted to an iron-containing protein composition solution by adding dextrin thereto.

Example 4

Solution M:

Fifteen liters of an aqueous solution containing 10 M of sodium bicarbonate.

Solution N:

Three liters of an aqueous solution containing 180 mM (as iron) of ferric chloride.

Solution O:

Twelve liters of an aqueous solution containing 1 mM (as a whey protein before enzyme hydrolysis) of a whey protein hydrolysis product.

In the solution O, adjustment of molar concentration was conducted using average molar weight. This average molecular weight was determined by examining the proportions of the individual protein components in the whey protein by sodium dodecyl sulfate (SDS)-polyacrylamide gel electrophoresis and making calculation using the proportions and the molecular weights of the individual protein components.

The whey protein hydrolysis product used in the solution O was produced as follows. That is, 1 kg of a whey protein (purity: 80%) concentrate (a product of New Zealand Daily Board) was dissolved in 19 kg of deionized water. The resulting solution was adjusted to pH 8. Thereto were added 2.4 l (400,000 units) of alcalase (a product of Novo Nordisk) and 4,000,000 units of actinase AS (a product of Kaken Pharmaceutical Co., Ltd.). The mixture was kept at 50° C. for 6 hours with the pH being maintained at 8, to give rise to hydrolysis. The reaction mixture was adjusted to pH 7, then heated at 90° C. for 10 minutes to deactivate the enzymes, and cooled. The resulting solution was passed through a filtration apparatus using an UF membrane (molecular weight cutoff: 3,000), to obtain a whey protein hydrolysis product.

The solution N (3 liters) and the solution O (12 liters) were mixed to prepare a mixed solution (N+O)(15 liters). This mixed solution (N+O) (15 liters) was added to the solution M (15 liters) to prepare a mixed solution (M+N+O). This mixed solution was heat-pasteurized at 90° C. for 10 minutes and then concentrated to 1/20 using a rotary evaporator (RE-10ED-120, a product of Shibata Kagaku) to obtain 600 g of a concentrate of an iron-containing protein composition solution. The concentrate was subjected to a homogenization treatment at 300 kg/cm$^2$. To 300 g out of 600 g was added 15 g of erythritol, and nothing was added to the remaining 300 g.

The thus-prepared two samples were stored in a frozen state at −20° C. for 2 weeks, then thawed at room temperature, and evaluated for freezing-thawing stability and measured for average particle diameter according to the same methods as in Example 1. The results are shown in Table 4.

TABLE 4

|  | Erythritol | No addition |
|---|---|---|
| Precipitate (ml) | 0.1 | 2.9 |
| Average particle diameter (nm) | 37.1 | 370.8 |

As is clear from the results of Table 4, it was confirmed that freezing-thawing stability can be imparted to an iron-containing protein composition solution by adding erythritol thereto.

Example 5

Solution P:

One liter of an aqueous solution containing 1,300 mM of sodium bicarbonate.

Solution Q:

0.2 liter of an aqueous solution containing 12 mM (as iron) of ferric sulfate.

Solution R:

0.8 liter of an aqueous solution containing 0.1 mM (as lactic acid casein before partial decomposition) of a lactic acid casein decomposition product.

In the solution R, adjustment of molar concentration was conducted using average molar weight. This average molecular weight was determined by examining the proportions of α-casein, β-casein and κ-casein by urea-sodium dodecyl sulfate (SDS) electrophoresis and making calculation using the proportions and the theoretical molecular weights of the individual caseins.

The lactic acid casein decomposition product used in preparation of the solution R was produced as follows. That is, there was prepared a solution containing 5% by weight of lactic acid casein (a product of New Zealand Daily Board). Thereto was added sodium bicarbonate for pH adjustment to 8.0. To the resulting solution was added 1,000 units (per g of casein) of trypsin (a proteolytic enzyme, a product of Novo Nordisk). While pH was being maintained at 8.0 by addition of sodium hydroxide, partial decomposition was conducted at 50° C. for 6 hours. The reaction mixture was kept at 85° C. for 20 minutes to deactivate the enzyme, whereby the partial decomposition was completed. The resulting solution was passed through a filtration apparatus using an UF membrane (molecular weight cutoff: 10,000), to obtain a lactic acid casein hydrolysis product.

The solution Q (0.2 liter) and the solution R (0.8 liter) were mixed to prepare a mixed solution (Q+R) (1 liter). This mixed solution (Q+R) (1 liter) was added to the solution P (1 liter) to prepare a mixed solution (P+Q+R). This mixed solution was heat-pasteurized at 65° C. for 30 minutes and then subjected to a homogenization treatment at 300 kg/cm$^2$ to obtain an iron-containing protein composition solution (1 liter). To 500 ml of the 1-l solution was added 50 g of trehalose, and nothing was added to the remaining 500 ml.

The thus-prepared two samples were each stored in a container in a frozen state at −20° C. for 2 weeks, then thawed by contacting the outer wall of the container with a flowing water, and evaluated for freezing-thawing stability and measured for average particle diameter according to the same methods as in Example 1. The results are shown in Table 5.

TABLE 5

|  | Trehalose | No addition |
|---|---|---|
| Precipitate (ml) | 0.1 | 1.8 |
| Average particle diameter (nm) | 34.9 | 360.2 |

As is clear from the results of Table 5, it was confirmed that freezing-thawing stability can be imparted to an iron-containing protein composition solution by adding trehalose thereto.

Example 6

Solutions having the following compositions were prepared.

Solution A:

16.5 kg of an aqueous solution containing 4% by weight (0.48 M) of sodium bicarbonate.

Solution B:

1.76 kg of an aqueous solution containing 10% by weight (1.25 mM) of lactoferrin Solution C:

24.31 kg of an aqueous solution (a product of Junsei Kagaku) containing 0.45% by weight (16.6 mM) of ferric chloride.

The solution A, the solution B and the solution C were mixed. The mixed solution was pasteurized until its temperature reached 90° C. The solution after sterilization was concentrated to 1/20 using a rotary evaporator (RE-10ED-120, a product of Shibata Kagaku). The resulting concentrate was subjected to a homogenization treatment at 300 kg/cm$^2$ using a homogenizer (GM-1, a product of K. K. SMT). To the homogenized concentrate was added 20% by weight of dextrin. One liter of the resulting mixture and 1 liter of the homogenized concentrate per se were each powderized using a spray drier (Pulvis Mini-Spray, GB-21). Using each of the resulting powders, 100 g of an aqueous solution containing 25% by weight of the powder was prepared.

The thus-prepared two samples (two solutions) were evaluated for freezing-thawing stability and measured for average particle diameter according to the same methods as in Example 1. The results are shown in Table 6.

TABLE 6

|  | Dextrin | No addition |
|---|---|---|
| Precipitate (ml) | 0.1 | 1.9 |
| Average particle diameter (nm) | 35.6 | 400.2 |

As is clear from the results of Table 6, it was confirmed that freezing-thawing stability can be imparted to an iron-containing protein composition solution by adding dextrin thereto.

What is claimed is:

1. An iron-containing protein composition solution comprising;
    an aqueous medium and an iron-containing protein composition dispersed in the aqueous medium, said iron-containing protein composition comprising (i) at least one of a carbonate or a bicarbonate; iron; and a protein; and (ii) at least one sugar compound selected from the group consisting of monosaccharides, disaccharides, sugaralcohols, non-reducing saccharides and dextrin in an amount of about 3% to about 50% by weight based on the weight of the aqueous medium including the iron-containing protein composition to provide said iron-containing protein composition solution with an excellent freezing-thawing stability,
    said iron-containing protein composition solution having a pH of about 5 to about 10.

2. The iron-containing protein composition solution according to claim 1, wherein said protein is at least one selected from the group consisting of lactoferrins, casein proteins and whey proteins.

3. A frozen product of an iron-containing protein composition solution set forth in claim 1 or 2.

4. A liquid composition obtained by thawing a frozen product set forth in claim 3.

5. A powder obtained by drying a liquid composition set forth in claim 4.

6. A method of preparing a powder comprising the step of drying the liquid composition of claim 4.

7. A powder obtained by drying of an iron-containing protein composition solution set forth in claim 2.

8. A method of preparing a powder comprising the step of drying of the iron-containing protein composition solution of claim 2.

9. A powder obtained by drying of an iron-containing protein composition solution set forth in claim 1.

10. A method of preparing a powder comprising the step of drying of the iron-containing protein composition solution of claim 1.

11. The iron-containing protein composition solution according to claim 1, wherein said iron-containing protein composition has an average particle size of about 50 nm or less.

12. A method of preparing an iron-containing protein composition solution including a sugar compound, which comprises the steps of:
    preparing an iron-containing composition solution comprising an aqueous medium and an iron-containing protein composition dispersed in the aqueous medium, said iron-containing protein composition comprising at least one of a carbonate or a bicarbonate, iron, and a protein; and
    adding at least one sugar compound selected from the group consisting of monosaccharides, disaccharides, sugaralcohols, non-reducing saccharides and dextrin in an amount of about 3% to about 50% by weight based on the weight of the aqueous medium including the iron-containing protein composition to provide said iron-containing protein composition solution with an excellent freezing-thawing stability, said iron-containing protein composition solution having a pH of about 5 to about 10.

13. The method of preparing an iron-containing protein composition solution according to claim 12, wherein said protein is at least one selected from the group consisting of lactoferrins, casein proteins and whey proteins.

14. A method of preparing a frozen product of an iron-containing protein composition solution comprising the step of freezing the iron-containing protein composition solution including a sugar compound of claim 13.

15. A method of preparing a liquid composition comprising the step of thawing a frozen product obtained by the method of claim 14.

16. The method of preparing an iron-containing protein composition solution according to claim 12, wherein said iron-containing protein composition has an average particle size of about 50 nm or less.

* * * * *